(12) United States Patent
Luyken et al.

US009914693B2

(10) Patent No.: US 9,914,693 B2
(45) Date of Patent: Mar. 13, 2018

(54) PROCESS FOR PREPARING EDA USING $SO_2$-FREE HYDROCYANIC ACID

(71) Applicant: BASF SE, Ludwigshafen (DE)

(72) Inventors: Hermann Luyken, Ludwigshafen (DE); Stephanie Jaegli, Mannheim (DE); Michael Lorenz, Ludwigshafen (DE); Gordon Brasche, Frankfurt (DE); Markus Jegelka, Mannheim (DE); Barbara Becker, Mannheim (DE); Robert Baumann, Mannheim (DE); Johann-Peter Melder, Boehl-Iggeelheim (DE); Boris Buschhaus, Heidelberg (DE); Thomas Krug, Worms (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/771,409

(22) PCT Filed: Feb. 12, 2014

(86) PCT No.: PCT/EP2014/052727
§ 371 (c)(1),
(2) Date: Aug. 28, 2015

(87) PCT Pub. No.: WO2014/131620
PCT Pub. Date: Sep. 4, 2014

(65) Prior Publication Data
US 2016/0009633 A1    Jan. 14, 2016

(30) Foreign Application Priority Data

Feb. 28, 2013 (EP) .................... 13157251

(51) Int. Cl.
*C07C 209/48* (2006.01)
*C07C 253/00* (2006.01)
*C07C 253/30* (2006.01)
*C07C 209/86* (2006.01)
*C07C 253/08* (2006.01)

(52) U.S. Cl.
CPC .......... *C07C 209/48* (2013.01); *C07C 209/86* (2013.01); *C07C 253/00* (2013.01); *C07C 253/08* (2013.01); *C07C 253/30* (2013.01)

(58) Field of Classification Search
CPC .... C07C 209/48; C07C 253/30; C07C 253/00
USPC ...................................... 564/490
See application file for complete search history.

(56) References Cited

U.S. PATENT DOCUMENTS

| | | | |
|---|---|---|---|
| 2,571,099 A | 10/1951 | Arthur, Jr. et al. | |
| 5,079,380 A * | 1/1992 | Thunberg | C07C 253/00 558/346 |
| 6,469,211 B2 | 10/2002 | Oftring et al. | |
| 7,915,454 B2 * | 3/2011 | Oftring | C07C 209/48 564/490 |
| 8,637,709 B2 | 1/2014 | Schaub et al. | |
| 8,785,693 B2 | 7/2014 | Schaub et al. | |
| 8,912,361 B2 | 12/2014 | Schaub et al. | |
| 8,946,459 B2 | 2/2015 | Luyken et al. | |
| 9,000,218 B2 | 4/2015 | Wigbers et al. | |
| 9,012,638 B2 | 4/2015 | Luyken et al. | |
| 9,096,497 B2 | 8/2015 | Luyken et al. | |
| 2006/0201798 A1 | 9/2006 | Bartsch et al. | |
| 2010/0094057 A1 | 4/2010 | Oftring et al. | |
| 2010/0099872 A1 | 4/2010 | Dahmen et al. | |
| 2010/0121109 A1 | 5/2010 | Dahmen et al. | |
| 2012/0245389 A1 | 9/2012 | Wigbers et al. | |
| 2012/0245390 A1 | 9/2012 | Wigbers et al. | |
| 2012/0253077 A1 | 10/2012 | Jodecke et al. | |
| 2013/0053536 A1 | 2/2013 | Luyken et al. | |
| 2013/0053538 A1 | 2/2013 | Luyken et al. | |
| 2013/0085286 A1 | 4/2013 | Luyken et al. | |

FOREIGN PATENT DOCUMENTS

| | | | |
|---|---|---|---|
| CN | 1771197 A | | 5/2006 |
| CN | 1858036 A | | 11/2006 |
| CN | 101622221 A | | 1/2010 |
| EP | 0742045 A1 | | 11/1996 |
| EP | 0963975 A1 | | 12/1999 |
| EP | 1209146 A1 | | 5/2002 |
| JP | 2006-523590 A | | 10/2006 |
| JP | 2010-520164 A | | 6/2010 |
| JP | 2010-520175 A | | 6/2010 |
| WO | 99/33561 | | 7/1999 |
| WO | 99/44984 | | 9/1999 |
| WO | 2004/092068 A1 | | 10/2004 |
| WO | 2008/104552 A1 | | 9/2008 |
| WO | 2008/104578 A1 | | 9/2008 |
| WO | 2008/104579 A1 | | 9/2008 |
| WO | 2008/104592 A1 | | 9/2008 |
| WO | 2011/067226 A1 | | 6/2011 |
| WO | 2012/119927 A1 | | 9/2012 |
| WO | 2012/119929 A1 | | 9/2012 |

(Continued)

OTHER PUBLICATIONS

Whiteford JK. The Impact of Aqueous Sulfur Dioxide Upon the Reactions and Availability of Hydrocyanic Acid and Formaldehyde on Prebiotic Earth. A Dissertation, University of California, Riverside. UMI Microform 3305666. Mar. 2008 (Year: 2008).*

(Continued)

*Primary Examiner* — Yih-Horng Shiao
(74) *Attorney, Agent, or Firm* — Oblon, McClelland, Maier & Neustadt, L.L.P.

(57) ABSTRACT

The present invention relates to a process for preparing ethylenediamine (EDA), where the process comprises the steps a) to c). In step a), formaldehyde is reacted with hydrocyanic acid (HCN) to form formaldehyde cyanohydrin (FACH), where the hydrocyanic acid is completely free or largely free of sulfur dioxide ($SO_2$). The FACH prepared in this way is reacted with ammonia ($NH_3$) to form aminoacetonitrile (AAN) in step b), whereupon a hydrogenation of AAN in the presence of a catalyst to form EDA is carried out in step c).

23 Claims, 1 Drawing Sheet

(56) References Cited

FOREIGN PATENT DOCUMENTS

| WO | 2012/119930 A1 | 9/2012 |
|---|---|---|
| WO | 2012/126869 A1 | 9/2012 |
| WO | 2012/126956 A1 | 9/2012 |
| WO | 2013/030023 A1 | 3/2013 |
| WO | 2013/030143 A1 | 3/2013 |
| WO | 2013/030161 A1 | 3/2013 |
| WO | 2013/030174 A1 | 3/2013 |
| WO | 2013/030249 A1 | 3/2013 |
| WO | 2013/030259 A1 | 3/2013 |
| WO | 2013/030287 A1 | 3/2013 |
| WO | 2013/104560 A1 | 7/2013 |

OTHER PUBLICATIONS

U.S. Appl. No. 61/529,314, filed Aug. 31, 2011, Robert Baumann, et al.
International Search Report dated May 6, 2014 in PCT/EP2014/052727 filed Feb. 12, 2014.
Office Action dated May 16. 2016, in Chinese Patent Application No. 201480010550.X (submitting English translation only).
English translation of Notification of Reasons for Refusal dated Sep. 26, 2016 in Japanese Patent Application No. 2015-559456.
Oxidation and Reduction (II), New Experiment Chemistry Lesson 15, Feb. 20, 1977, pp. 409-411 (with partial English language translation).

* cited by examiner

PROCESS FOR PREPARING EDA USING $SO_2$-FREE HYDROCYANIC ACID

The present invention relates to a process for preparing ethylenediamine (EDA), where the process comprises the steps a) to c). In step a), formaldehyde is reacted with hydrocyanic acid (HCN) to form formaldehyde cyanohydrin (FACH), where the hydrocyanic acid is completely free or largely free of sulfur dioxide ($SO_2$). The FACH prepared in this way is reacted with ammonia ($NH_3$) to form aminoacetonitrile (AAN) in step b), whereupon a hydrogenation of AAN in the presence of a catalyst to form EDA is carried out in step c).

Processes for preparing EDA have been known for a long time, and hydrocyanic acid is frequently used as one of the starting materials for this purpose. WO 2008/104578discloses a process for preparing an ethylene amine mixture comprising EDA, in which crude AAN which is largely free of formaldehyde cyanohydrin is heated at a temperature of from 50 to 150° C. This gives an aminonitrile mixture comprising AAN and iminodiacetonitrile (IDAN). This mixture is subsequently hydrogenated in the presence of a catalyst to give EDA and diethylenetriamine (DETA). WO 2008/104578 further discloses that the crude AAN used can be obtained by reacting an aqueous mixture of ammonia with FACH in a molar ratio of ≥4:1 [mol/mol] at a temperature of from 50 to 80° C.

The preparation of formaldehyde cyanohydrin (FACH) has likewise been known for a long time. Detailed information on the preparation of FACH from formaldehyde and hydrocyanic acid may be found, for example, in WO 2008/104579. However, in this process, the FACH is not used for preparing EDA via AAN by reaction with ammonia, but instead FACH is reacted there with EDA to give ethylenediaminediacetonitrile (EDDN). EDDN can in turn be hydrogenated to triethylenetetramine (TETA).

The hydrocyanic acid used for the preparation of FACH in practice always comprises acidic stabilizers such as sulfuric acid, phosphoric acid, acetic acid and in particular sulfur dioxide ($SO_2$). Particularly in the presence of alkalis (for example when stored in glass vessels), hydrocyanic acid slowly polymerizes with precipitation of blackish-brown flocs or undergoes an autocatalytical polymerization which, particularly in industrial processes, leads to blockage of pipes. This polymerization method of hydrocyanic acid is prevented by addition of acidic stabilizers, in particular $SO_2$ (see also Römpp Chemielexikon, $9^{th}$ edition 1995, Georg-Thieme-Verlag Stuttgart; and also WO 2004/092068).

WO 2004/092068 relates to a method of purifying hydrocyanic acid by distillation and also a process for the hydrocyanation of olefins or dienes. In this process, the watering of hydrocyanic acid is carried out by distillation of aqueous crude hydrocyanic acid having an HCN content of not more than 99.9% by weight. The crude hydrocyanic acid can optionally also comprise carbon oxides and a nonvolatile stabilizer. The crude hydrocyanic acid is distilled in the absence of a volatile stabilizer at a pressure of from 1 to 2.5 bar, a temperature at the bottom of from 100 to 130° C. and a temperature at the top of from 25 to 54° C. in a distillation column. The purified anhydrous hydrocyanic acid can be obtained from the overhead offtake stream. Any nonvolatile or relatively nonvolatile stabilizers comprised are, in contrast, separated off via the bottom offtake of the distillation column. Suitable nonvolatile stabilizers for dewatering the crude hydrocyanic acid are, for example, sulfuric acid and phosphoric acid which are used instead of volatile stabilizers such as sulfur dioxide in the process according to WO 2004/092068. However, WO 2004/092068 gives no indication that the hydrocyanic acid which has been purified in this way and consequently also freed of the added stabilizers can be used in any form together with formaldehyde for preparing FACH and also for the further conversion into AAN and/or EDA.

WO 2008/104552 relates to a process for preparing an ethylene amine mixture, in which an aminonitrile mixture comprising at least two alpha-aminonitriles in an amount of at least 5% by weight is hydrogenated in the presence of a catalyst and optionally a solvent. As alpha-aminonitrile, it is possible to use, inter alia, AAN, as a result of which EDA can be present in the ethylene amine mixture. The AAN can in turn be prepared from FACH, which is obtained by reaction of formaldehyde and hydrocyanic acid, and ammonia. As in the case of WO 2008/104579, WO 2008/104552 gives no suggestion that the hydrocyanic acid used is free of acidic stabilizers, in particular free of sulfur dioxide.

WO 2011/067226 relates to a process for distilling a mixture comprising water, ethylenediamine and N-methylethylenediamine, in which the mixture is introduced into a distillation column which is operated at a pressure at the top of from 10 mbar to 4 bar. Water and ethylenediamine have to be present in a particular ratio in this mixture. The mixture used for the distillation is once again a reaction output obtained by reaction of formaldehyde, hydrocyanic acid, ammonia and hydrogen.

The international application PCT/EP2012/066808 discloses a process for preparing amines of a general formula (II) by hydrogenation of the corresponding nitriles in the presence of a catalyst in the suspension mode or in a fixed bed at a specific space velocity over the catalyst. If $R^1$ is hydrogen in the formula (II), the corresponding amine is EDA which is accordingly obtained by hydrogenation of AAN. However, the process according to PCT/EP2012/066808 leads first and foremost to the preparation of TETA and DETA from the corresponding nitriles EDDN and EDMN, respectively. The preparation of the nitriles EDDN and EDMN can in turn be carried out from formaldehyde and hydrocyanic acid via the intermediate FACH. An acidic stabilizer, for example sulfur dioxide, sulfuric acid, phosphoric acid or an organic acid such as acetic acid, is generally added to the hydrocyanic acid used in order to prevent the autocatalytic polymerization of hydrocyanic acid, which can lead to blockages in pipes.

The international application PCT/EP2012/066833 discloses a further process for preparing TETA and/or DETA by reacting EDDN and/or EDMN with hydrogen in the presence of a catalyst. As catalyst, use is made of a catalyst of the Raney type, and the pressure in the hydrogenation is in the range from 170 to 240 bar. However, no nitriles other than AAN are subjected to a hydrogenation in this process.

It is therefore an object of the present invention to provide a novel process for preparing ethylenediamine (EDA).

The object is achieved by a process for preparing ethylenediamine (EDA), which comprises the steps a) to c):
  a) reaction of formaldehyde and hydrocyanic acid (HCN) to form formaldehyde cyanohydrin (FACH), where the hydrocyanic acid is completely free or largely free of sulfur dioxide ($SO_2$),
  b) reaction of FACH with ammonia ($NH_3$) to form aminoacetonitrile (AAN),
  c) hydrogenation of AAN in the presence of a catalyst to give EDA.

A substantial advantage of the process of the invention is that the operating life of the hydrogenation catalyst (i.e. the catalyst which is used in step c)) is improved. This effect is apparent particularly when the hydrocyanic acid used for the preparation of FACH in step a) is completely or at least largely free of sulfur dioxide and also optionally of further acidic stabilizers such as sulfuric acid or phosphoric acid.

The use of (largely) $SO_2$-free hydrocyanic acid in step a) thus has, in particular, a positive effect on the performance of the hydrogenation catalyst used in step c). The hydrogenation of AAN can thus be carried out over long periods of time to give high EDA yields without a significant decrease in the catalyst activity. $SO_2$ in particular tends to disproportionate in the presence of the catalyst under the process conditions customary in a nitrile hydrogenation, forming, inter alia, sulfides which contribute significantly to reducing the performance of a hydrogenation catalyst. Such a disproportionation is, on the other hand, not observed or observed to only a significantly reduced extent when using sulfuric acid instead of $SO_2$.

In addition, the yields of the substeps are also positively influenced by the use of (largely) $SO_2$-free hydrocyanic acid in step a), which in turn has an effect on the total EDA yield.

A further advantage of the process of the invention is the flexibility. The process of the invention can be carried out batchwise, in the semibatch mode and in particular continuously for preparing EDA from formaldehyde, hydrocyanic acid and also ammonia and hydrogen. Furthermore, the optional work-up steps to be carried out in the process of the invention are advantageous both in terms of apparatus and energy consumption.

Furthermore, it is advantageous in the process of the invention when the hydrocyanic acid is used in a slightly substoichiometric amount relative to formaldehyde in step a) and/or, in step b), ammonia is used in a large molar excess over the FACH prepared in step a). Furthermore, it is advantageous for the pressure in step b) to be selected so that it is slightly higher than in the subsequent hydrogenation in step c), since a transport device (e.g. a pump) can be omitted as a result.

A further advantage can be achieved if the excess or unreacted ammonia used in step b) is separated off from the reaction mixture (hydrogenation product) after the hydrogenation in step c) and is recirculated. The ammonia is advantageously separated off in two stages, with the isolation of ammonia or ammonia recovery being able to be operated efficiently by means of appropriate pressure and temperature regulation, for example in the form of a closed condensation.

For the purposes of the present invention, the expression "largely free of sulfur dioxide" has the following meaning: the sulfur dioxide content of the hydrocyanic acid used is less than 200 ppm by weight, preferably less than 100 ppm by weight, more preferably less than 50 ppm by weight and in particular less than 30 ppm by weight. The above figures are based on the amount of hydrocyanic acid used.

Furthermore, for the purposes of the present invention, the expression "completely free of sulfur dioxide" has the following meaning: the sulfur dioxide content of the hydrocyanic acid used is less than 10 ppm by weight, preferably less than 1 ppm by weight, in particular less than 0.1 ppm by weight. The above figures are based on the amount of hydrocyanic acid used.

Analogous statements in respect of the content of other stabilizers also apply, for the purposes of the present invention, to the embodiments in which the hydrocyanic acid is completely or largely free of other acidic stabilizers such as sulfuric acid, phosphoric acid or acetic acid.

The present invention will be described in more detail below.

In the process of the invention, the reaction of formaldehyde and hydrocyanic acid (HCN) to form formaldehyde cyanohydrin (FACH), where the hydrocyanic acid is completely free or largely free of sulfur dioxide ($SO_2$), is carried out in step a).

Formaldehyde is a chemical which is generally available in commerce. Formaldehyde is preferably used in the form of an aqueous solution. The formaldehyde is preferably aqueous formaldehyde having a formaldehyde content of from 20 to 60% by weight [mol/mol], particularly preferably a formaldehyde content of from 25 to 55% by weight.

Hydrocyanic acid is likewise a chemical which is generally available in commerce. Hydrocyanic acid can be prepared industrially by essentially three different processes. In a first process, hydrocyanic acid can be obtained by ammoxidation of methane by means of oxygen and ammonia (Andrussov process). In a second process, hydrocyanic acid can be obtained from methane and ammonia by ammodehydrogenation in the presence of oxygen. Finally, hydrocyanic acid can be prepared industrially by dehydration of formamide.

Hydrocyanic acid can be used in liquid or gaseous form, as a pure substance or as an aqueous solution. Preference is given to using hydrocyanic acid as from 50 to 100% strength by weight, particularly preferably as from 75 to 100% strength by weight, aqueous solution. Hydrocyanic acid is preferably used in a purity of 90% by weight or more.

As indicated above (including the specifical numerical values), the hydrocyanic acid can be completely free or largely free of sulfur dioxide ($SO_2$) for the purposes of the process of the invention. Sulfur dioxide can be added directly as stabilizer to the hydrocyanic acid (for example after its production). A person skilled in the art will know that $SO_2$ forms sulfurous acid ($H_2SO_3$) in the presence of water. Measurement methods for determining the $SO_2$ content of hydrocyanic acid are known to those skilled in the art; for example, the determination can be carried out by means of ion chromatography.

Since commercially available hydrocyanic acid generally comprises stabilizers, in particular acidic stabilizers, the present invention is either carried out using freshly synthesized and thus stabilizer-free hydrocyanic acid or the stabilizers present, in particular sulfur dioxide, are removed by methods known to those skilled in the art immediately before use in step a). Stabilizer-free hydrocyanic acid can be prepared by distillation from hydrocyanic acid comprising nonvolatile stabilizers, in particular sulfuric acid or phosphoric acid, by the methods described in WO 2004/092068. Here, the hydrocyanic acid is distilled off at the top and the corresponding stabilizers are obtained as bottom products.

Stabilizer-free hydrocyanic acid can, according to U.S. Pat. No. 2,571,099, be obtained from hydrocyanic acid comprising volatile stabilizers, in particular sulfur dioxide, by passing an inert gas through the hydrocyanic acid.

In a preferred embodiment of the present invention, hydrocyanic acid which is completely free or largely free of stabilizers is used in step a). The numerical values corresponding to the terms "completely free" or "largely free" have been defined above. In this context, sulfur dioxide, sulfuric acid, phosphoric acid, acetic acid, oxalic acid and possibly other acids which are known to those skilled in the art as acidic stabilizers for hydrocyanic acid are, in particular, regarded as stabilizers.

The reaction of formaldehyde, preferably aqueous formaldehyde, and hydrocyanic acid to form FACH can be carried out batchwise, in the semibatch mode or continuously. It is preferably carried out in a backmixed reactor with removal of heat, for example using a heat exchanger. As reactors for carrying out step a), it is possible to use, in particular, stirred reactors, loop reactors or tube reactors.

Step a) can in principle be carried out at any temperatures; the reaction temperature is preferably from 0 to 70° C., more preferably from 10 to 50° C., particularly preferably from 10 to 45° C.

The pressure in step a) is selected so that the reaction mixture is present in liquid form.

The hydrocyanic acid is preferably used in an equimolar or slightly substoichiometric amount relative to formaldehyde. The molar ratio of HCN to formaldehyde is more preferably from 0.85 to 1.0:1 [mol/mol], even more preferably from 0.9 to 1.0:1 [mol/mol], in particular from 0.95 to 1.0:1 [mol/mol].

Furthermore, the reaction mixture is preferably set to a pH of from 3.5 to 6.5, preferably from 4.0 to 6.0, particularly preferably 5.5, by means of a base, preferably sodium hydroxide.

The residence time in the FACH synthesis is from 1 minute to 1 hour, preferably from 5 minutes to 30 minutes.

The HCN conversion in the FACH synthesis is >99% (determined by Volhard titration), and the FACH yield is >98% (determined by combined Volhard and Liebig titration).

If the preferably aqueous FACH solution obtained is to be concentrated to, for example, a from 50 to 80% strength by weight solution, it is advantageous to reduce the pH of the reaction mixture of step a) to values of <5.5, preferably <3.5. This can be achieved, for example, by addition of mineral acids such as sulfuric acid or phosphoric acid.

In step b) of the process of the invention, FACH is reacted with ammonia ($NH_3$) to form aminoacetonitrile (AAN).

According to the invention, the reaction output from step a), i.e. the FACH or a mixture comprising FACH, is generally reacted without work-up and without the additional use of a solvent, with ammonia to form AAN. In step b), ammonia can be used not only as starting material in the preparation of AAN but also as solvent. An aqueous FACH solution obtained in step a) can optionally be concentrated by evaporation of water.

The reaction of FACH with ammonia can be carried out batchwise, in the semibatch mode or continuously. The reaction can be carried out in any suitable apparatus known to those skilled in the art. An adiabatic or cooled flow tube without backmixing or a reactor having plug flow characteristics is preferably used in step b). In this way, the formation of troublesome secondary components from FACH and AAN, recognizable by the color, can be avoided.

In step b), the temperature is generally from 0 to 150° C., preferably from 50 to 100° C., particularly preferably from 70 to 90° C.

In step b), the pressure can in principle be set to any desired value. The pressure in step b) is preferably from 20 to 400 bar, in particular from 80 to 270 bar. The pressure in step b) is preferably so high that the reaction mixture is liquid. Furthermore, the pressure in step b) is preferably higher than in step c). For example, the pressure in step b) can be from 5 to 20 bar higher than in step c).

The molar ratio of FACH to ammonia can in principle have any desired value, but at least an equimolar amount of ammonia is generally used; ammonia is preferably used in a high molar excess over FACH. The molar ratio of FACH to ammonia in step b) is preferably from 1:2 to 1:15 [mol/mol], more preferably from 1:5 to 1:30 [mol/mol], in particular from 1:10 to 1:20 [mol/mol].

The residence time of the reaction mixture in the respective apparatus is preferably from 0.1 to 20 minutes, particularly preferably from 1.0 to 10 minutes.

The AAN yield is (based on FACH) preferably ≥95%. Furthermore, the weight ratio of AAN to IDAN is preferably 99:1.

In step b), the reaction output preferably comprises from 10 to 50% by weight of AAN, from 10 to 80% by weight of ammonia, <1% by weight of FACH, <1% by weight of IDAN. The balance is water which is formed in step b) in the preparation of AAN or has been introduced, together with the starting materials, in the preparation of FACH.

In a preferred embodiment of the present invention, the AAN obtained in step b) is
 i) hydrogenated, as crude AAN in step c) without prior work-up by distillation and/or without removal of water, or
 ii) subjected to an adsorptive purification using an ion exchanger or a metal oxide before being hydrogenated in step c).

In step c) of the process of the invention, the hydrogenation of AAN is carried out in the presence of a catalyst to give ethylenediamine (EDA).

The hydrogenation to give EDA is generally carried out by reacting AAN with hydrogen in the presence of the catalyst ("hydrogenation catalyst"). Here, at least two mole of hydrogen are required per mole of AAN. The AAN obtained in step b) can be subjected directly to the hydrogenation in step c), but further work-up steps can optionally be carried out between step b) and step c), as explained below.

The hydrogen is generally used in technical-grade purity. The hydrogen can also be used in the form of a hydrogen-comprising gas, i.e. in admixture with other inert gases such as nitrogen, helium, neon, argon or carbon dioxide. As hydrogen-comprising gases, it is possible to use, for example, reformer offgases, refinery gases, etc., when and insofar as these gases do not comprise any catalyst poisons for the hydrogenation catalysts used, for example CO. However, preference is given to using pure hydrogen or essentially pure hydrogen in the process, for example hydrogen having a content of more than 99% by weight of hydrogen, preferably more than 99.9% by weight of hydrogen, particularly preferably more than 99.99% by weight of hydrogen, in particular more than 99.999% by weight of hydrogen.

As catalysts, it is in principle possible to use all catalysts known to a person skilled in the art for nitrile hydrogenation. Thus, for example, it is possible to use catalysts comprising one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species as catalysts for the hydrogenation (hydrogenation catalysts) of the nitrile function of AAN.

These include skeletal catalysts (also referred to as Raney® type; hereinafter also:

Raney catalyst) which are obtained by leaching (activation) of an alloy of a hydrogenation-active metal and a further component (preferably Al). The catalysts can additionally comprise one or more promoters.

In a particularly preferred embodiment, Raney catalysts, preferably Raney cobalt or Raney nickel catalysts and particularly preferably a Raney cobalt catalyst which comprises at least one of the elements Ni, Cr or Fe as promoter, are used in the hydrogenation of AAN. The Raney cobalt catalyst is thus doped with at least one of these elements. According to the invention, the Raney catalysts are preferably used as suspended Raney catalysts.

The catalysts can be used as all-active catalysts or in supported form. As supports, preference is given to using metal oxides such as $Al_2O_3$, $SiO_2$, $ZrO_2$, $TiO_2$, mixtures of metal oxides or carbon (activated carbons, carbon blacks, graphite).

The catalysts used for the hydrogenation can be activated by methods known to those skilled in the art, for example outside a reactor or in the reactor, before use. A special position in activation is occupied by the skeletal catalysts which can be activated by leaching with an aqueous base, as described, for example, in EP-A 1 209 146. Depending on the process carried out (suspension hydrogenation, fluidized-bed process, fixed-bed hydrogenation), the catalysts are used as powder, crushed material or shaped bodies (preferably extrudates or pellets).

Particularly preferred fixed-bed catalysts are the all-active cobalt catalysts which are disclosed in EP-A1 742 045 and are doped with Mn, P and alkali metal (Li, Na, K, Rb, Cs). The catalytically active composition of these catalysts comprises, before reduction by means of hydrogen, from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts which are disclosed in EP-A 963 975 and whose catalytically active composition before treatment with hydrogen comprises from 22 to 40% by weight of $ZrCO_2$, from 1 to 30% by weight of oxygen-comprising compounds of copper, calculated as CuO, from 15 to 50% by weight of oxygen-comprising compounds of nickel, calculated as NiO, where the molar ratio of Ni:Cu is greater than 1, 15 to 50% by weight of oxygen-comprising compounds of cobalt, calculated as CoO, from 0 to 10% by weight of oxygen-comprising compounds of aluminum and/or of manganese, calculated as $Al_2O_3$ or $MnO_2$, and no oxygen-comprising compounds of molybdenum, for example the catalyst A which is disclosed in this document and has the composition 33% by weight of Zr, calculated as $ZrO_2$, 28% by weight of Ni, calculated as NiO, 11% by weight of Cu, calculated as CuO, and 28% by weight of Co, calculated as CoO.

Further suitable catalysts are those disclosed in EP-A 696 572, whose catalytically active composition before reduction by means of hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or of manganese, calculated as $Al_2O_3$ or $MnO_2$; for example the catalyst specifically disclosed in this document having the composition 31.5% by weight of $ZrO_2$, 50% by weight of NiO, 17% by weight of CuO and 1.5% by weight of $MoO_3$. The catalysts which are described in WO-A-99/44984 and comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight, based on (a), of a compound based on an alkali metal and/or alkaline earth metal and also (d) from 0.001 to 1% by weight, based on (a), of manganese, are also suitable.

In the case of suspension processes, Raney catalysts are preferably used. In the Raney catalysts, the active catalyst is produced as "metal sponge" from a binary alloy (nickel, iron, cobalt, with aluminum or silicon) by leaching out a partner by means of acid or alkali. Residues of the original alloying partner often act synergetically.

The Raney catalysts used in the process of the invention are preferably produced from an alloy of cobalt or nickel, particularly preferably cobalt, and a further alloying component which is soluble in alkalis. Aluminum is preferably used as this soluble alloying component, but it is also possible to use other components such as zinc and silicon or mixtures of such components.

To activate the Raney catalyst, the soluble alloying component is completely or partly extracted by means of alkali, for which purpose it is possible to use, for example, aqueous sodium hydroxide. The catalyst can then be washed with, for example, water or organic solvents.

Individual or a plurality of further elements can be present as promoters in the catalyst. Examples of promoters are metals of transition groups IB, VIB and/or VIII of the Periodic Table, e.g. chromium, iron, molybdenum, nickel, copper etc. Activation of the catalysts by leaching out of the soluble component (typically aluminum) can be carried out either in the reactor itself or before introduction into the reactor. The preactivated catalysts are air-sensitive and pyrophoric and are therefore generally stored and handled under a medium such as water, an organic solvent or a material which is present in the reaction according to the invention (solvent, starting material, product) or embedded in an organic compound which is solid at room temperature.

In a preferred embodiment, a Raney cobalt skeletal catalyst which has been obtained from a Co/Al alloy by leaching with aqueous alkali metal hydroxide solution, e.g. sodium hydroxide solution, and subsequent washing with water and preferably comprises at least one of the elements Fe, Ni or Cr as promoters is used for the purposes of the invention.

Such catalysts typically comprise, in addition to cobalt, 1-30% by weight of Al, in particular 2-12% by weight of Al, very particularly preferably 3-6% by weight of Al, 0-10% by weight of Cr, in particular 0.1-7% by weight of Cr, very particularly preferably 0.5-5% by weight of Cr, more particularly 1.5-3.5% by weight of Cr, 0-10% by weight of Fe, in particular 0.1-3% by weight of Fe, very particularly preferably 0.2-1% by weight of Fe, and/or 0-10% by weight of Ni, in particular 0.1-7% by weight of Ni, very particularly preferably 0.5-5% by weight of Ni, more particularly 1-4% by weight of Ni, where the percentages by weight are in each case based on the total weight of the catalyst.

A cobalt skeletal catalyst "Raney 2724" from W. R. Grace & Co can, for example, be advantageously used as catalyst in the process of the invention. This catalyst has the following composition:

Al: 2-6% by weight, Co: 86% by weight, Fe: 0-1% by weight, Ni: 1-4% by weight, Cr: 1.5-3.5% by weight.

A nickel skeletal catalyst which has been obtained from an Ni/Al alloy by leaching with aqueous alkali metal hydroxide solution, e.g. sodium hydroxide solution, and subsequent washing with water and preferably comprises at least one of the elements Fe, Cr as promoters can likewise be used for the purposes of the invention.

Such catalysts typically comprise, in addition to nickel, 1-30% by weight of Al, in particular 2-20% by weight of Al, very particularly preferably 5-14% by weight of Al, 0-10% by weight of Cr, in particular 0.1-7% by weight of Cr, very particularly preferably 1-4% by weight of Cr, and/or 0-10% by weight of Fe, in particular 0.1-7% by weight of Fe, very particularly preferably 1-4% by weight of Fe, where the percentages by weight are in each case based on the total weight of the catalyst.

A nickel skeletal catalyst A 4000 from Johnson Matthey can, for example, be advantageously used as catalyst in the process of the invention. This catalyst has the following composition:

Al: <14% by weight, Ni: ≥80% by weight, Fe: 1-4% by weight, Cr: 1-4% by weight.

The catalysts can optionally be regenerated by methods known to those skilled in the art, as disclosed, for example, in WO 99/33561 and the documents cited therein, when the activity and/or selectivity decreases.

The regeneration of the catalyst can be carried out in the actual reactor (in situ) or on the catalyst removed from the reactor (ex situ). In the case of fixed-bed processes, regeneration is preferably carried out in situ, while in the case of suspension processes, preference is given to removing part of the catalyst either continuously or discontinuously, regenerating it ex situ and returning it.

In step c), the space velocity over the catalyst is preferably from 0.1 to 3 gram of AAN per gram of catalyst an hour, preferably from 0.2 to 1.5 gram of AAN per gram of catalyst an hour, in particular from 0.4 to 1.2 gram of AAN per gram of catalyst an hour.

Furthermore, preference is given in step c) to the catalyst having a BET surface area of from 10 to 100 $m^2$ per gram of catalyst, preferably from 20 to 500 $m^2$ per gram of catalyst, in particular from 30 to 100 $m^2$ per gram of catalyst. The measurement for determining the BET surface area is known to those skilled in the art, and the BET method in accordance with DIN 66131 is generally employed for this purpose.

The hydrogenation can in principle be carried out at any temperatures; the hydrogenation is preferably carried out at a temperature of from 20 to 150° C., more preferably from 40 to 120° C., particularly preferably at from 70 to 110° C.

In principle, any pressure can be employed in the hydrogenation; the pressure in the hydrogenation is preferably from 40 to 400 bar, more preferably from 80 to 300 bar, particularly preferably from 100 to 270 bar.

The AAN is preferably fed to the hydrogenation at a rate which is not greater than the rate at which the AAN reacts with hydrogen in the hydrogenation. The feed rate is preferably set so that effectively full conversion is achieved. This is influenced by pressure, temperature, amount and type of catalyst, amount of AAN in the mixture fed in, the quality of mixing of the contents of the reactor and the residence time, etc.

The reaction of AAN with hydrogen in the presence of catalysts can be carried out continuously, in the semibatch mode or discontinuously in conventional reaction vessels suitable for catalysis using a fixed-bed, fluidized-bed or suspension mode of operation. Reaction vessels with which the AAN and the catalyst can be brought into contact with the hydrogen under superatmospheric pressure are suitable for carrying out the hydrogenation.

The hydrogenation in the suspension mode of operation can be carried out in a stirred reactor, jet loop reactor, jet nozzle reactor, bubble column reactor or in a cascade of identical or different reactors of this type.

Preference is given to using jet loop reactors having an external circuit in which the heat of reaction can be removed by cooling.

For the purposes of the present invention, a jet loop reactor is a reactor provided with a nozzle at which a jet which introduces gaseous hydrogen into the liquid is generated. The nozzle is operated using the starting material streams, preferably using an external liquid circuit, particularly preferably using starting materials and the external liquid circuit. In a preferred variant, an additional tube which prevents momentum exchange is comprised in the reactor, so that an internal circuit can be formed.

The hydrogenation over a fixed-bed catalyst preferably takes place in one or more tube reactors or else shell-and-tube reactors.

The catalyst can be present in suspended form or in the form of extrudates or pellets. Preference is given to a suspended catalyst which is retained in the reactor by filtration using candle filters or crossflow filtration. The crossflow filtration is particularly preferably realized in the external circuit stream of a jet loop reactor.

The hydrogenation of the nitrile groups takes place with liberation of heat which generally has to be removed. The removal of heat can be effected by means of built-in heat exchanger surfaces, cooling jackets or external heat exchangers in a circuit around the reactor. The hydrogenation reactor or a cascade of hydrogenation reactors can be operated in a single pass. A recycle mode of operation in which part of the reactor output is recirculated to the reactor inlet, preferably without prior work-up of the circuit stream, is also alternatively possible.

In particular, the circuit stream can be cooled in a simple and inexpensive way by means of an external heat exchanger and the heat of reaction can thus be removed.

The reactor can also be operated adiabatically. In adiabatic operation of the reactor, the temperature rise in the reaction mixture can be limited by cooling of the feed streams or by introduction of "cold" organic solvent. As an alternative, cooling can be effected by deliberately allowing vaporization/evaporation of the solvent within the reactor to occur.

Since the reactor itself then does not have to be cooled, a simple and inexpensive type of construction is possible. An alternative is a cooled shell-and-tube reactor (only in the case of a fixed bed). A combination of the two modes of operation is also conceivable. Here, a fixed-bed reactor is preferably installed downstream of a suspension reactor.

The catalyst can be arranged in a fixed bed (fixed-bed mode) or be suspended in the reaction mixture (suspension mode).

In a particularly preferred embodiment, the catalyst is suspended in the reaction mixture to be hydrogenated.

The settling rate of the hydrogenation catalyst in the solvent selected should be low so that the catalyst can readily be kept in suspension.

The particle size of the catalysts used is therefore preferably in the range from 0.1 to 500 μm, in particular from 1 to 100 μm, in the case of the suspension mode of operation.

If the hydrogenation of AAN in the suspension mode is carried out continuously, AAN is preferably fed continuously to the reactor and a stream comprising the hydrogenation product EDA is continuously removed from the reactor.

The amount of catalyst in the case of the discontinuous suspension mode is preferably from 1 to 60% by weight, particularly preferably from 5 to 40% by weight and very particularly preferably from 20 to 35% by weight, based on the total reaction mixture.

The catalyst concentration in a continuously operated reactor is from 1 to 60%, preferably from 5 to 40%, particularly preferably from 20 to 35% by weight.

The residence time in the reactor in the discontinuous suspension mode is preferably from 0.1 to 6 hours, particularly preferably from 0.5 to 2 hours.

The residence time in the reactor in the continuous suspension mode is preferably from 0.1 to 6 hours, particularly preferably from 0.5 to 2 hours.

If the reaction in the suspension mode is carried out in a stirred reactor, the power input via the stirrer is preferably from 0.1 to 100 kW per $m^3$, preferably from 1 to 10 kW/$m^3$.

Exhausted catalyst can be separated off by filtration, centrifugation or crossflow filtration. Here, it can be necessary to make up losses of originally introduced catalyst due to abrasion and/or deactivation by addition of fresh catalyst.

After the hydrogenation, the output from the hydrogenation can optionally be purified further. The catalyst can be separated off by methods known to those skilled in the art. In general, the hydrogen present during the hydrogenation is separated off after the catalyst has been separated off.

Hydrogen is preferably separated off by reducing the pressure at which the hydrogenation was carried out to a value at which hydrogen is gaseous but the other components in the reaction output are present in the liquid phase. The reaction output is preferably depressurized from a hydrogenation pressure of preferably from 60 to 325 bar, particularly preferably from 100 to 280 bar and very particularly preferably from 170 to 240 bar, to a pressure of from 5 to 50 bar into a vessel. Hydrogen, possibly ammonia, and possibly small amounts of vaporized low boilers or solvents are obtained at the top of the vessel. Hydrogen and optionally ammonia can be recirculated to the hydrogenation of AAN.

The hydrogenation output comprises firstly the target product EDA. Unreacted starting material in the form of AAN or precursors thereof may possibly also be comprised in the hydrogenation output. AAN is preferably no longer comprised in the hydrogenation output. In general, the hydrogenation output comprises not only EDA but also ammonia and water which were used in the preceding process stages, for example as starting material or solvent, and/or have been formed. Diethylenetriamine (DETA) and possibly N-methylethylenediamine (N-MEDA) are generally formed as by-product in the hydrogenation of AAN. According to the invention, the hydrogenation output comprises EDA together with from 1 to 10% of DETA and from 1 to 5% of N-MEDA, based on the solvent-free EDA.

The yield of target product EDA is preferably from 85 to 100%, more preferably from 90 to 100%.

After the hydrogenation in step c) of the process of the invention, EDA is preferably separated off from the hydrogenation product. EDA is preferably separated off by distillation using methods known to those skilled in the art. Furthermore, preference is given to carrying out the isolation of EDA after the ammonia removal described below in step d) and/or the removal of water. An isolation of EDA by distillation is particularly preferably carried out only after the ammonia removal as per step d) and subsequently the removal of water have firstly been carried out.

In a preferred embodiment of the present invention, a removal of ammonia from the hydrogenation product is carried out as step d) after the hydrogenation in step c). The removal of ammonia from the hydrogenation product is preferably carried out before a removal of water and isolation of EDA by distillation are carried out. The ammonia separated off in step d) is particularly preferably recirculated to step b). The recirculated ammonia is preferably mixed with fresh ammonia and subsequently fed together into the apparatus for carrying out step b).

Furthermore, step d) is preferably carried out in two stages, with ammonia being taken off at from 20 to 70° C. at the top of a column (K1) and condensed out in a first stage in which the temperature at the bottom is less than 220° C. and an $NH_3$-depleted stream is transferred from the bottom to a second column (K2) and, in the second stage, EDA being separated off at the bottom of the second column (K2), where the EDA is (largely) free of ammonia, and an $NH_3$-comprising stream optionally being recirculated to the column (K1).

As columns (K1) and (K2), it is possible to use all distillation apparatuses known to those skilled in the art for this purpose. In column (K1), the temperature at the top of the column ("condensation temperature") is preferably from 20 to 70° C., in particular from 35 to 60° C. The temperature in the column (K1), especially in the top region, is preferably regulated via the pressure. The pressure can be determined by means of vapor pressure tables for ammonia which are known to those skilled in the art. The temperature at the bottom of the column (K1) is preferably <200° C., particularly preferably <190° C. The temperature at the bottom is preferably set via the ammonia content which is taken off from the bottom of the column (K1). In general, the temperature at the bottom will not be less than 140° C.

In the second stage, the column pressure is preferably set so that the output from the bottom of the column (K2) is ammonia-free or largely free of ammonia. The output from the bottom is considered to be largely free of ammonia when the ammonia content is <1% by weight, preferably <0.5% by weight, while the output from the bottom is considered to be ammonia-free when the ammonia content is <0.1% by weight, preferably 0.01% by weight.

The temperatures at the bottom of the column (K2) correspond to the temperatures at the bottom which have been indicated above in connection with the column (K1). Ammonia is separated off from the upper part of the column (K2), preferably via the top of the column. This stream preferably comprises not only ammonia but also water. The water content is preferably set so that the temperature at the top of the column (K2) or the condensation temperature corresponds to the temperature ranges at the top of the column indicated above for the column (K1). The $NH_3$-comprising stream which is preferably taken off from the top of the column (K2) and additionally comprises water is preferably returned to the column (K1) for the first stage of the ammonia removal. The condenser is particularly preferably operated in the form of a closed condensation. This can be effected by backmixing of the condensate (introduction of a circuit via the condenser) or by condensation in co-current.

In a further embodiment of the present invention, water is separated off from the hydrogenation product after the hydrogenation in step c); the removal of water is preferably carried out after the ammonia removal as per step d).

Figure 1:
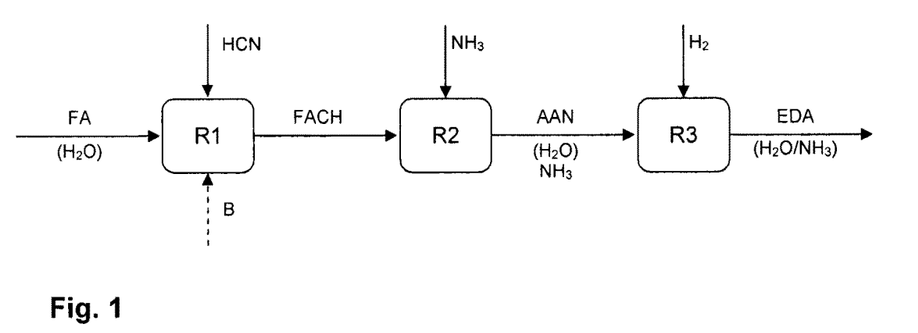
FIG. 1: A schematic of the process of the invention, where "FA" is formaldehyde, "B" is base, and "R1" to "R3" are reactors.

The process of the invention will be illustrated once more in its basic form in FIG. 1. "FA" is formaldehyde, "B" is base. The use of a base is merely optional here, as is indicated by the broken line. Process steps a) to c) are preferably carried out in corresponding reactors which are analogously designated as "R1" to "R3" in FIG. 1. The main components (starting materials or products) of the respective steps are correspondingly indicated using arrows; the most important by-products and unreacted starting materials of the individual steps are indicated in parentheses. Any further work-up steps or specific embodiments of the respective apparatuses, for example the use of two hydrogenation reactors connected in series for step c), are not schematically shown in FIG. 1 but can optionally be additionally carried out or be present.

Figure 2:
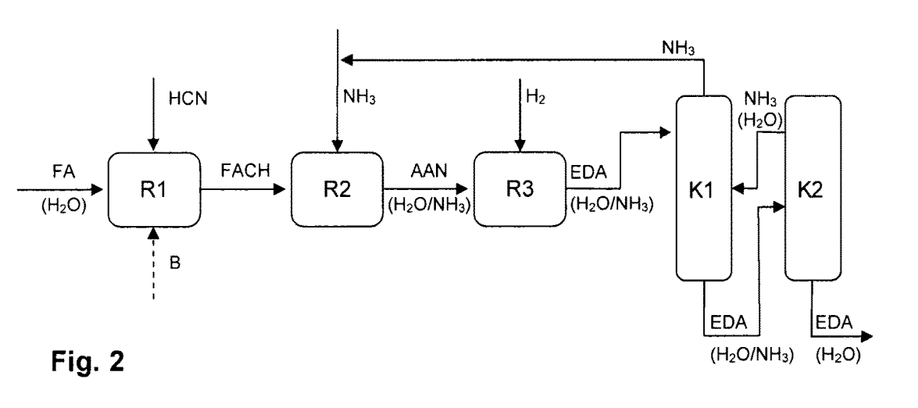
FIG. 2: A schematic of a preferred embodiment of the invention, where the abbreviations are the same as in FIG. 1 and "K1" and "K2" designate the columns used for the respective stages.

A preferred embodiment of the present invention is additionally shown in FIG. 2. In FIG. 2, the abbreviations, arrows and other symbols have meanings analogous to those indicated above for FIG. 1. Compared to the embodiment in FIG. 1, a removal and recirculation of ammonia (as per step d)) is additionally carried out in the embodiment of FIG. 2. The ammonia removal can, as shown in FIG. 2, preferably be carried out in two stages. "K1" and "K2" here designate the columns used for the respective stages. Furthermore, preference is given to a removal of water being additionally carried out in this embodiment. The removal of water can, for example, be carried out before or after the ammonia removal, and the removal of water is preferably carried out after the ammonia removal.

The invention is illustrated below with the aid of examples.

EXAMPLE 1

Synthesis of Formaldehyde Cyanohydrin (Fach)

7000 g (70 mol) of formaldehyde (30% strength) are placed in a 10 l reaction vessel provided with a propeller stirrer and a pH of 5.5 inset by means of sodium hydroxide solution (1 mol/l). 1870 g (68.3 mol) of hydrocyanic acid ($SO_2$ content 30 ppm) are introduced in gaseous form via a heated U-tube underneath the stirrer over a period of 3.5 hours, with the reaction temperature being maintained at 30° C. and the pH being maintained at 5.5. After stirring for a further 30 minutes, the pH is brought to 2.5 by means of sulphuric acid (50% strength). The FACH content is determined by Liebig titration (about 44% strength).

EXAMPLE 2

Synthesis of Crude Alpha-aminoacetonitrile (AAN)

Formaldehyde cyanohydrin (FACH, about 44% strength, 380.8 g/h, prepared as described in example 1) is reacted with liquid ammonia (489 g/h) in a molar ratio of 1:10 in a tube reactor (40 ml, external diameter 3.17 mm) at 90° C. and 80 bar. The residence time in the reactor is 2 minutes. Downstream of the reactor, the mixture is cooled to 10° C. and depressurized in a flash vessel, with excess ammonia being partly removed. The reaction output is free of FACH (determination by Liebig titration). Crude AAN is obtained as an aqueous solution (yield of AAN based on FACH: >98%; ratio of AAN to IDAN: >99:1). Yield and selectivity are determined by means of quantitative HPLC (stationary phase: 3×Atlantis T3, 5 µm, 250 mm×4.6 mm, Waters; mobile phase: 50% by volume of water/50% by volume of acetonitrile with 0.5 g/l of ammonium formate; flow: 0.8 ml/min).

EXAMPLE 3

Hydrogenation of Crude AAN

The continuous hydrogenation of AAN (prepared as described in example 2) is carried out in a 270 ml autoclave provided with baffles and disk stirrer. For this purpose, 10 g of an aqueous suspension of a Cr-doped Raney cobalt catalyst (Ra-Co 2724, from Grace) (corresponding to 5 g of dry catalyst) are placed in the autoclave, 15 standard l/h of hydrogen are introduced continuously and the autoclave is brought to 100° C. At 180 bar, 18 g/h of a 27% strength crude AAN solution in water/ammonia and 40 g/h of pure ammonia are then fed in. The suspension catalyst is retained in the reactor by means of a filter element made of sintered metal.

Over a period of 588 hours, the yield of EDA decreases from 96.1% to 91.1%, while the yield of DETA increases from 1.1% to 4.1%. The Me-EDA yield is constant at 3.6-3.7%.

Analysis: analysis of the reaction output is carried out by means of GC using factorized % by area.
Column: RTX-5 Amine, 30 m, 0.25 mm, 1.0 µm
Temperature program: 60° C.—5 min isothermal—15° C./min—280° C.
Sulfur content of the catalyst: 0.2 atom % of $S^{2-}$ and 0.3 atom % of $S^{6+}$ on the surface, determined by XPS

EXAMPLE 4

Hydrogenation of Crude AAN with Subsequent Addition of Sulfur (Comparison)

The continuous hydrogenation of AAN (prepared by the method of example 2) is carried out in a 270 ml autoclave provided with baffles and disk stirrer. For this purpose, 10 g of an aqueous suspension of a Cr-doped Raney cobalt catalyst (Ra-Co 2724, from Grace) (corresponding to 5 g of dry catalyst) are placed in the autoclave, 15 standard l/h of hydrogen are continuously introduced and the autoclave is brought to 100° C. The suspension catalyst is retained in the reactor by means of a filter element made of sintered metal. At 180 bar, 18 g/h of a 27% strength crude AAN solution in water/ammonia and 40 g/h of pure ammonia are then fed in. After a running time of 60 hours under these conditions, the EDA content in the output is 95.3%, that of DETA is 1.8% and that of Me-EDA is 2.5%. From a running time of 60 hours, about 50 ppm of sulfur in the form of $H2SO_3$ are added as 6% strength aqueous solution to the crude AAN feed. After 40 hours under these conditions, the EDA content in the output decreases to 17% and the output still comprises 19% of AAN.

Analysis: the analysis of the reaction output is carried out by means of GC using factorized % by area.
Column: RTX-5 Amine, 30 m, 0.25 mm, 1.0 µm
Temperature program: 60° C.—5 min isothermal—15° C./min—280° C.

The invention claimed is:
1. A process for preparing ethylenediamine (EDA), comprising:
   a) reacting a mixture of formaldehyde and hydrocyanic acid (HCN) to form formaldehyde cyanohydrin (FACH), wherein a sulfur dioxide content of the hydrocyanic acid used is less than 100 ppm by weight based on an amount of hydrocyanic acid used, and wherein the mixture has a pH of from 3.5 to 6.5;

b) reacting the FACH with ammonia (NH$_3$) to form aminoacetonitrile (AAN); and c) hydrogenating the AAN in the presence of a catalyst to yield a hydrogenation product comprising the EDA.

2. The process according to claim 1, wherein in a), the molar ratio of HCN to formaldehyde is 0.85 to 1.00:1 or the formaldehyde is an aqueous formaldehyde having a formaldehyde content of 20% to 60% by weight.

3. The process according to claim 1, wherein in b), the molar ratio of FACH to ammonia is 1:2 to 1:50.

4. The process according to claim 1, wherein the pressure in b) is so high that a reaction mixture formed in b) is in liquid.

5. The process according to claim 1, wherein the catalyst is a Raney catalyst.

6. The process according to claim 1, wherein in c) hydrogenating step, the space velocity over the catalyst is 0.1 gram to 3 grain of AAN per gram of the catalyst an hour.

7. The process according to claim 1, wherein the catalyst has a BET surface area of 10 m$^2$ to 100 m$^2$ per gram of the catalyst.

8. The process according to claim 1, wherein in c) hydrogenating step, the temperature is 20° C. to 150° C. or the pressure is 40 bar to 400 bar.

9. The process according to claim 1, wherein, the AAN formed in b) is
   i) hydrogenated in c) without prior work-up by distillation and/or without removal of water, or
   ii) subjected to an adsorptive purification with an ion exchanger or a metal oxide before being hydrogenated in c).

10. The process according to claim 1, further comprising:
    d) removing ammonia from the hydrogenation product after c).

11. The process according to claim 10, wherein d) is carried out in two stages, wherein:
    in the first stage, ammonia is taken off at 20° C. to 70° C. at the top of a first column and condensed out to produce an NH$_3$-depleted stream and an NH$_3$-comprising stream, and the NH$_3$-depleted stream is transferred from the bottom of the first column having a temperature of less than 220° C. to a second column,
    in the second stage, EDA is separated from the NH$_3$-depleted stream at the bottom of the second column and the NH$_3$-comprising stream is optionally recirculated to the first column, wherein the EDA contains 1% by weight or less of ammonia.

12. The process according to claim 10, wherein the ammonia removed is recirculated from d) to b).

13. The process according to claim 1, further comprising:
    removing water from the hydrogenation product after c).

14. The process according to claim 1, further comprising:
    separating the EDA from the hydrogenation product by distillation after c).

15. The process according to claim 1, wherein the catalyst is a Raney cobalt catalyst comprising: Al: 2-6% by weight, Co: ≤86% by weight, Fe: 0-1% by weight, Ni: 1-4% by weight, and Cr: 1.5-3.5% by weight.

16. The process according to claim 1, wherein the pressure in b) reacting step is higher than the pressure in c) hydrogenating step.

17. The process according to claim 5, wherein the Raney catalyst is a Raney nickel catalyst or a Raney cobalt catalyst.

18. The process according to claim 17, wherein the Raney cobalt catalyst comprises one or more promoters selected from the group consisting of Fe, Ni and Cr.

19. The process according to claim 1, wherein the catalyst has a BET surface of 20 m$^2$ to 500 m$^2$ per gram of the catalyst.

20. The process according to claim 10, further comprising:
    removing water from the hydrogenation product after d).

21. The process according to claim 10, further comprising:
    separating the EDA from the hydrogenation product by distillation after d).

22. The process according to claim 1, wherein the HCN has a sulfur dioxide content of less than 10 ppm.

23. The process according to claim 1, wherein the b) reacting step is carried out at a temperature of 50-150° C. and a residence time of 1 to 10 minutes.

* * * * *